United States Patent [19]
Yang et al.

[11] Patent Number: 5,858,676
[45] Date of Patent: Jan. 12, 1999

[54] ELECTROCHEMILUMINESCENCE OF RARE EARTH METAL CHELATES

[75] Inventors: Hongjun Yang, Rockville; Nicholas Cairns, Gaithersburg, both of Md.

[73] Assignee: IGEN International, Inc., Gaithersburg, Md.

[21] Appl. No.: 891,337

[22] Filed: Jul. 10, 1997

Related U.S. Application Data

[63] Continuation of Ser. No. 423,394, Apr. 18, 1995, abandoned.

[51] Int. Cl.$^6$ .................................................. G01N 33/53
[52] U.S. Cl. ............................... 435/6; 435/7.1; 435/7.2; 436/501; 436/518; 436/537; 436/82; 436/172; 436/806
[58] Field of Search ................................ 435/4, 5, 6, 7.1, 435/7.2, 7.9, 7.92, 7.93, 7.94, 7.95, 240.1, 243; 436/501, 518, 536, 537, 543, 544, 149, 150, 151, 172, 800, 806, 81, 82; 530/300, 350; 536/1.11, 22.1; 252/700

[56] References Cited

U.S. PATENT DOCUMENTS

| | | | |
|---|---|---|---|
| 3,700,410 | 10/1972 | Sievers | 436/173 |
| 4,205,952 | 6/1980 | Cais | 436/518 |
| 4,290,815 | 9/1981 | Henry | 106/200.3 |
| 4,293,310 | 10/1981 | Weber | 436/536 |
| 4,372,745 | 2/1983 | Mandle et al. | 436/537 |
| 5,147,806 | 9/1992 | Kamin et al. | 436/149 |
| 5,310,687 | 5/1994 | Bard et al. | 436/518 |

FOREIGN PATENT DOCUMENTS 2217007  10/1989  United Kingdom .

OTHER PUBLICATIONS

Bogulaski and Li "Homogenous Immunoassays", 7 Applied Biochemistry and Biotechnology 401–414 (1982).

*Primary Examiner*—Lora M. Green
*Attorney, Agent, or Firm*—Whitman Breed Abbott & Morgan, LLP

[57] ABSTRACT

Luminescent chemical reagents that include complexes of rare earth metals with ligands such as aromatic heterocyclic nitrogen-containing compounds and semi-aromatic oxygen-containing compounds are used to detect small quantities of complex substances such as pharmaceuticals, metabolites, and microorganisms in complex sample mixtures.

15 Claims, 1 Drawing Sheet

ELECTROCHEMILUMINESCENCE OF RARE EARTH METAL CHELATES

This application is a continuation of application Ser. No. 08/423,394, filed Apr. 18, 1995 now abandoned.

FIELD OF THE INVENTION

The present invention relates to luminescent metal chelate labels for use in qualitative and quantitative chemical analysis. More specifically, the present invention relates to the use of chemical reagents that include complexes of rare earth metals with ligands such as aromatic heterocyclic nitrogen-containing compounds and semi-aromatic oxygen-containing compounds to detect small quantities of complex substances such as pharmaceuticals, metabolites, and microorganisms.

BACKGROUND OF THE INVENTION

There is a continuous and expanding need for rapid, highly specific methods of detecting and quantifying chemical, biochemical, and biological substances. Of particular value are methods for measuring small quantities of pharmaceuticals, metabolites, microorganisms, and other materials of diagnostic value. Examples of such materials include narcotics and poisons, drugs administered for therapeutic purposes, hormones, pathogenic microorganisms and viruses, antibodies, metabolites, enzymes and nucleic acids.

The presence of these materials can often be determined by binding methods which exploit the high degree of specificity which characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which has been attached to one or more of the complexing materials.

The specific labeling method chosen often dictates the usefulness and versatility of a particular system for detecting a material of interest. A preferred label should be inexpensive, safe, and capable of being attached efficiently to a wide variety of chemical, biochemical, and biological materials without changing the important binding characteristics of those materials. The label should give a highly characteristic signal, and should be rarely, and preferably never, found in nature. The label should be stable and detectable in aqueous systems over periods of time ranging from hours to months. Detection of the label should be rapid, sensitive, and reproducible without the need for expensive, specialized facilities or personnel. Quantification of the label should be relatively independent of variables such as temperature and the composition of the mixture to be assayed. Most advantageous are labels which can be used in homogeneous systems, i.e., systems in which separation of the complexed and uncomplexed labeled material is not necessary. This is possible if the detectability of the label is modulated when the labeled material is incorporated into a specific complex.

A wide variety of labels have been developed, each with particular advantages and disadvantages. For example, radioactive labels are quite versatile, and can be detected at very low concentrations. However, they are expensive, hazardous, and their use requires sophisticated equipment and trained personnel. Furthermore, the sensitivity of radioactive labels is limited by the fact that the detectable event can, in its essential nature, occur only once per radioactive atom in the labeled material. Moreover, radioactive labels cannot be used in homogeneous methods.

Thus, there is wide interest in non-radioactive labels. These include molecules observable by spectrophotometric, spin resonance, and luminescence techniques, as well as enzymes which produce such molecules. Among the useful non-radioactive labeling materials are organometallic compounds. Because of the rarity of some metals in biological systems, methods which specifically assay the metal component of the organometallic compounds can be successfully exploited. For example, Cais, U.S. Pat. No. 4,205,952 (1980) discloses the use of immunochemically active materials labeled with certain organometallic compounds for use in quantitating specific antigens. Any general method of detecting the chosen metals can be used with these labels, including emission, absorption and fluorescence spectroscopy, atomic absorption, and neutron activation. These methods often suffer from lack of sensitivity, can seldom be adapted to a homogeneous system, and as with atomic absorption; sometimes entail destruction of the sample.

Of particular interest are labels which can be made to luminesce through photochemical, chemical, and electrochemical means. "Photoluminescence" is the process whereby a material is induced to luminesce when it absorbs electromagnetic radiation. Fluorescence and phosphorescence are types of photoluminescence. "Chemiluminescent" processes entail the creation of the luminescent species by a chemical transfer of energy. "Electrochemiluminescence" entails the creation of the luminescent species electrochemically.

These luminescent items are of increasing importance. For example, Mandle, U.S. Pat. No. 4,372,745 (1983) discloses the use of chemiluminescent labels in immunochemical applications. In the disclosed systems, the labels are excited into a luminescent state by chemical means such as by reaction of the label with $H_2O_2$ and an oxalate. In these systems, $H_2O_2$ oxidatively converts the oxalate into a high energy derivative, which then excites the label. This system will, in principle, work with any luminescent material that is stable in the oxidizing conditions of the assay and can be excited by the high energy oxalate derivative. Unfortunately, this very versatility is the source of a major limitation of the technique; typical biological fluids containing the analyte of interest also contain a large number of potentially luminescent substances that can cause high background levels of luminescence.

Another example of the immunochemical use of chemiluminescence which suffers from the same disadvantages is Oberhardt et al., U.S. Pat. No. 4,290,815, (1981) who disclose the in situ electrochemical generation of an oxidant (e.g., $H_2O_2$) in close proximity to an immunoreactant labeled with a chemiluminescent species. The electrogenerated oxidant diffuses to the chemiluminescent species and chemically oxidizes it, resulting in the net transfer of one or more electrons to the electrogenerated oxidant. Upon oxidation, the chemiluminescent species emits a photon. In contrast, the subject invention requires the direct transfer of electrons from a source of electrochemical energy to a chemiluminescent species which is capable of repeatedly emitting photons.

The present invention is concerned with electrochemiluminescent labels. Suitable labels comprise electrochemiluminescent compounds, including organic compounds and organometallic compounds. Electrochemiluminescent methods of determining the presence of labeled materials are preferred over other methods for many reasons. They are highly diagnostic of the presence of a particular label, sensitive, nonhazardous, inexpensive, and can be used in a wide variety of applications.

Organic compounds which are suitable electrochemical labels include, for example, rubrene and 9,10-diphenyl anthracene. Many organometallic compounds are suitable electrochemical labels. For instance, Bard et al., in U.S. Pat. No. 5,310,687 (1994), discloses that a wide variety of analytes of interest and chemical moieties that bind to analytes of interest may be conveniently attached to ruthenium- or osmium-containing labels through amide or amine linkages. The labeled materials may then be determined by any of a wide variety of means, including photoluminescent, chemiluminescent, and electrochemiluminescent means. It is also disclosed therein that electrochemiluminescent labels, including ruthenium- and osmium-containing labels and organic molecules such as rubrene and 9,10-diphenyl anthracene, are particularly versatile and advantageous.

The series of elements having Atomic Numbers in the range 57–71 are known as the lanthanides; they are: cerium, dysprosium, erbium, europium, gadolinium, holmium, lanthanum, lutetium, neodymium, praseodymium, promethium, terbium, thulium, and ytterbium. The lanthanides are classically referred to as the 'rare earths'. They are also referred to as the inner-transition elements, because outer electron structure is identical across the group; their electron structures differ only at an inner level. Since the electronic diversity between the atoms is at some depth, the elements are very similar chemically. All of the lanthanides form trivalent ions and complexes. Their absorption bands are narrow compared with those of the normal transition ions. Complexing agents, which alter the absorption spectra of normal transition ions by modifying their outer electron structures, have little effect on the lanthanide ions. In spite of a high charge, lanthanide ions are too large to cause significant polarization, so complex formation is not facile.

With the transition metal chelates, the center metal atoms are unfulfilled d-orbitals. Under the ligand field, d-orbitals interact with the ligand field leading to splitting the d-orbitals into two different energy levels, which correspond to the ground state and to an excited state. Unlike the case with transition metals, rare earth metals have unfulfilled f-orbitals. The emission of rare earth metal chelates is due to the intromolecular energy transfer from the ligand to the metal ion. Therefore, the emission is more characteristic of the metal than of the interaction between the metal and its ligands.

The rare earth metal chelated usually have eight coordination sites rather than six as for transition metal chelates. The eight coordination sites are arranged as four in one plane and the other four in another plane, with the metal located between the planes. However, the two planes twist 45° with respect to each other, so this type of compound is not of an octahedral configuration.

The Bard et al. chemical moieties as disclosed in U.S. Pat. No. 5,310,687 do have one characteristic that constitutes a drawback in certain circumstances. The emission spectra of their chelates has a band width on the order of 100 nm. This can make signal discrimination difficult in multiple wavelength electrochemiluminescence measurements. Thus there remains a need for improvement in this area.

SUMMARY OF THE INVENTION

It has now been discovered that rare earth metal chelates may be prepared that have emission spectra band widths of less than 50 nm. The great advantages of the use of the novel labeled materials based upon the rare earth metal chelates, and of the methods of detecting them, follows.

According to the present invention there is provided a chemical moiety having the formula $[MPL^1L^2\text{-}(\text{-link-})\text{-}]_tB$ wherein M is a lanthanide element; P is a polydentate ligand of M; $L^1$ and $L^2$ are ligands of M, each of which may be a substance covalently bound to one or more of P, $L^1$, or $L^2$ through one or more covalent bond linkages such as amide and amine linkages, said linkages designated as (-link-) and linking B with at least one of P, $L^1$, or $L^2$; t is an integer equal to or greater than 1; and B is a substance of interest.

The present invention provides compounds particularly suitable as intermediates for attaching a luminescent lanthanide-containing label to amino groups of chemical, biochemical, and biological substances. These intermediates are thus particularly suitable for creating chemical moieties according to the present invention. The intermediates are the mono-and di-N-hydroxysuccinimide esters of lanthanide bis(2,2'-bipyridine)(2,2'-bipyridine-4,4'-dicarboxylic acid) and their salts and ruthenium or osmium bis(2,2'-bipyridine) (4,4'-di(chloromethyl)-2,2'-bipyridine). These compounds are generally synthesized by procedures which are known in the art.

The present invention provides methods for determining the presence of the novel chemical moieties. The present invention also provides methods of determining the presence of a chemical moiety as described above. The methods comprise:

a) forming a reagent mixture under suitable conditions containing the chemical moiety;

b) inducing the moiety to emit electromagnetic radiation by exposing the reagent mixture to chemical energy or electrochemical energy; and c) detecting the emitted electromagnetic radiation and thereby determining the presence of the chemical moiety.

This invention further provides for the use of lanthanide-containing labels in binding methods for determining the presence of substances of interest. These methods may be used to determine labeled moieties of interest, to employ labeled moieties to determine analytes of interest, or to use labelled analogues of analytes of interest to determine analytes of interest in competitive binding assays. These binding methods may be homogeneous or heterogeneous binding methods.

Still further, the present invention provides systems for determining the presence of the lanthanide-containing chemical moieties of this invention. These systems comprise a means for inducing the chemical moiety to emit electromagnetic radiation.

The present invention also provides for use of electrochemiluminescent labels in binding methods for determining the presence of substances of interest. These methods can be used to determine labeled moieties of interest, to employ labeled moieties to determine analytes of interest, or to use labeled analogues of analytes of interest to determine analytes of interest in competitive binding assays. These binding methods can be homogeneous or heterogeneous binding methods.

A specific embodiment of the invention provides for compositions which contain two or more different chemical moieties. Each of the moieties may be chemical species which can be induced to emit electromagnetic radiation of different wavelength. In another embodiment of the invention the chemical moieties may be chemical species each of which is induced to emit electromagnetic radiation by exposure to energy of a different value or from a different source. A different substance or analyte of interest may then be specifically attached to each of the different chemical moieties. By using these compositions and methods it is possible to determine two or more different substances or analytes of interest that may be present in the sample under examination.

DETAILED DESCRIPTION OF THE INVENTION

Figure 1A:
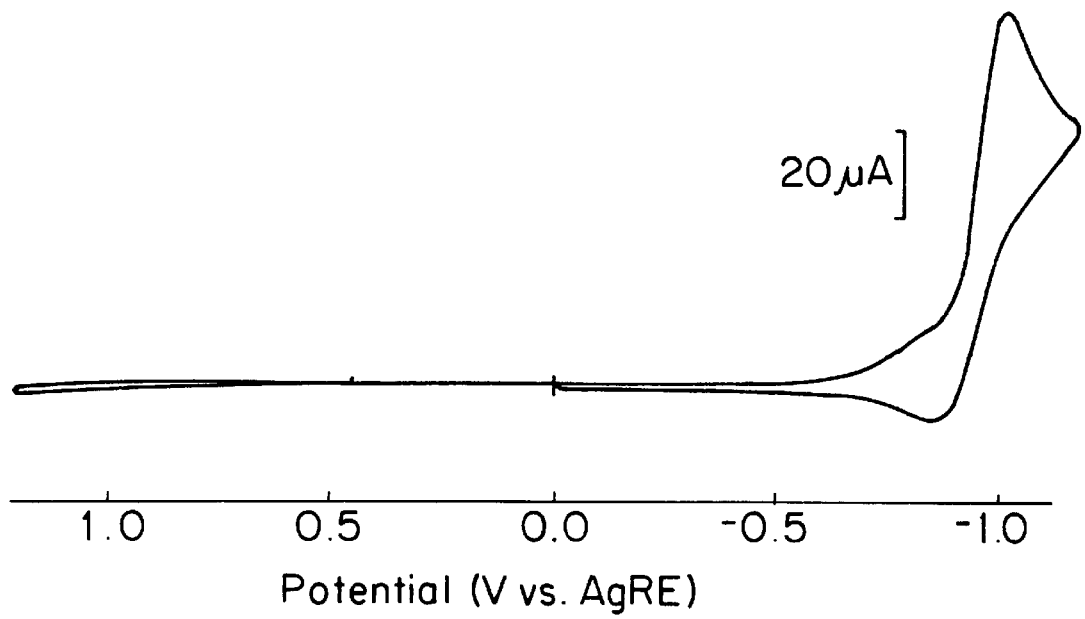
FIG. 1(a) shows a cyclic voltammogram for 2 mM europium chelate in 0.1M tetrabutylammonium hexafluorophosphate (hereinafter "TBAPF$_6$") acetonitrile solution.

The chemical moiety: M and its ligands

According to the present invention, there is provided a chemical moiety having the formula

[MPL$^1$L$^2$-(-link-)-]$_t$B wherein M is a lanthanide; P is a polydentate ligand of M; L$^1$ and L$^2$ are ligands of M, each of which may be a substance covalently bound to one or more of P, L$^1$, or L$^2$ through one or more amide or amine linkages; t is an integer equal to or greater than 1; P, L$^1$, L$^2$, and B are of such number that the total number of bonds to M provided by the ligands of M equals the coordination number of M; (-link-) designates the bond or bonds that connect B to P, L$^1$, and L$^2$; and P, L$^1$, L$^2$, and B are of such composition that the chemical moiety can be induced to emit electromagnetic radiation.

In accordance with the present invention, M may be cerium, dysprosium, erbium, europium, gadolinium, holmium, lanthanum, lutetium, neodymium, praseodymium, promethium, terbium, thulium, or ytterbium. In the currently preferred embodiments of the present invention, M is cerium, europium, terbium, or ytterbium, with europium being most preferred.

The chemical moiety in accordance with the present invention should have at least one polydentate ligand of M. When the moiety has more than one polydentate ligand, the polydentate ligands may be the same or different. Polydentate ligands include aromatic and aliphatic ligands. Suitable aromatic polydentate ligands include aromatic heterocyclic ligands such as, for example, bipyridyl, bipyrazyl, terpyridyl, phenanthrolyl, and porphyrins, as well as semi-aromatic oxygen-containing compounds such as, for example, diketone-type compounds. The semi-aromatic oxygen-containing compounds are currently preferred.

Suitable polydentate ligands may be unsubstituted, or substituted by any of a large number of substituents known to the art. Suitable substituents include for example, alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureido, maleimide, sulfur-containing groups, phosphorus containing groups, and the carboxylate ester of N-hydroxysuccinimide.

Additionally, at least one of L$^1$ and L$^2$ may be a polydentate aromatic heterocyclic ligand that contains nitrogen as well as semi-aromatic oxygen-containing compounds such as, for example, diketone-type compounds. The semi-aromatic oxygen-containing compounds are currently preferred. Suitable polydentate ligands include, but are not limited to, bipyridyl, bipyrazyl, terpyridyl, phenanthroyl, a porphyrin, substituted bipyridyl, substituted bipyrazyl, substituted terpyridyl, substituted phenanthroyl, or a substituted porphyrin. These nitrogen-containing aromatic ligands as well the semi-aromatic oxygen-containg ligands may be substituted with an alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureido, maleimide, a sulfur-containing group, a phosphorus-containing group, or the carboxylate ester of N-hydroxysuccinimide.

In one embodiment of the invention the chemical moiety contains two bidentate ligands, each of which is bipyridyl, bipyrazyl, terpyridyl, phenanthrolyl, substituted bipyridyl, substituted bipyrazyl, substituted terpyridyl, or substituted phenanthrolyl. In another embodiment of the invention the chemical moiety contains three bidentate ligands, each of which is bipyridyl, bipyrazyl, terpyridyl, phenanthrolyl, substituted bipyridyl, or substituted phenanthrolyl, for instance

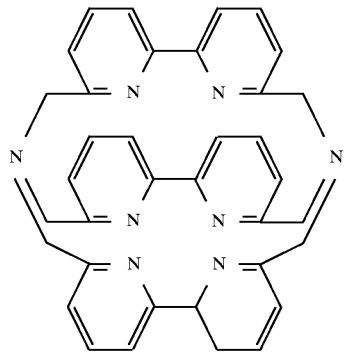

This chemical moiety may have one or more monodentate ligands, a wide variety of which are known to the art. Suitable monodentate ligands include, for example, carbon monoxide, cyanides, isocyanides, halides, and aliphatic, aromatic and heterocyclic phosphines, amines, stibines, and arsines.

In still another embodiment of the invention the chemical moiety contains a tetradentate ligand such as a porphyrin or substituted porphyrin, or mixed nitrogen-containing and oxygen-containing ligands, for instance

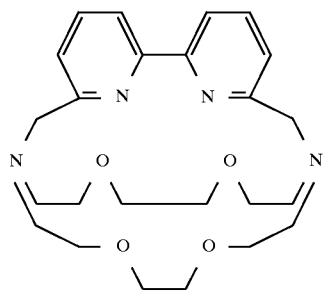

In a preferred embodiment of the invention, the chemical moiety contains three semi-aromatic oxygen-containing diketone-type ligands.

Preferred embodiments of this chemical moiety comprise bis(2,2'-bipyridyl)europium(II), tris(2,2'-bipyridyl)- europium(II), europium tris(1,1,1,2,2,3,3-heptafluoro-7,7-dimethyl-4,6-octanedionate), which has the structure

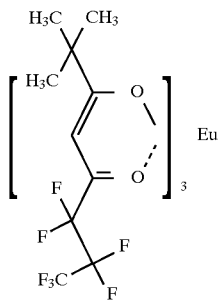

and terbium tris(2,2,6,6-tetramethyl-3,5-heptanedionate), which has the structure

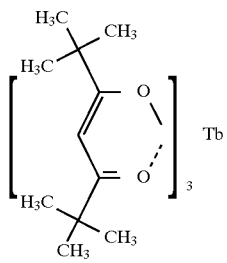

Some of these chelates are known. The others can be prepared by procedures analogous to those used for preparing the known species. U.S. Pat. No. 3,700,410 discloses the preparation of certain preferred chelates that may be used in accordance with the present invention. The entire disclosure of that patent is expressly incorporated herein by reference.

It is within the scope of the invention for one or more of the ligands of M to be attached to additional chemical labels, such as, for example, radioactive isotopes, fluorescent components, or additional luminescent europium-containing centers.

The chemical moiety: biological and nonbiological substances B

Suitable substances (B) include many biological substances, for example, whole cells, viruses, subcellular particles, proteins, lipoproteins, glycoproteins, peptides, nucleic acids polysaccharides, lipopolysaccharides, lipids, fatty acids, cellular metabolites, hormones, pharmacological agents, tranquilizers, barbiturates, alkaloids, steroids, vitamins, amino acids and sugars. Whole cell may be animal, plant, or bacterial, and may be viable or dead. Examples include plant pathogens such as fungi and nematodes. Within this application the term "subcellular particles" means subcellular organelles, membrane particles as from disrupted cells, fragments of cell walls, ribosomes, multienzyme complexes, and other particles which can be derived from living organisms. Also, within this application, nucleic acids means chromosomal rNA, plasmid rNA, viral rNA, and recombinant INA derived from multiple sources. Nucleic acids also include RiAs, for example messenger RiAs, ribosomal IRNAs and transfer RNAS. Polypeptides include, for example, enzymes, transport proteins, receptor proteins and structural proteins such as viral coat proteins. Preferred polypeptides are enzymes and serum-derived antibodies. Particularly preferred polypeptides are monoclonal antibodies. Thus, in one embodiment of the invention, B is a nucleotide or a polynucleotide. In another embodiment, B is a serum-derived antibody or a monoclonal antibody.

Hormones include, for example, insulin and T4 thyroid hormone. Pharmacological agents include, for example, cardiac glycosides. It is also within the scope of this invention of include synthetic nucleic acids, and synthetic membranes, vesicles and liposomes. The foregoing is not intended to be a comprehensive list of the biological substances suitable for use in this invention, but is meant only to illustrate the wide scope of the invention.

It is within the scope of this invention to include labeled nonbiological substances, including polymeric materials. These substances may be in the form of soluble polymeric molecules, or any of the large variety of known macroscopic forms such as, for example, beads, or containers such as test tubes, bottles, assay wells or the like.

The chemical moiety: linkages

Biological and nonbiological substances (B) are covalently bound to a ligand of M through one or more covalent linkages. These are designated as (-link-) in the formula set forth above and in the claims. Any type of covalent attachment is intended to be covered by the general term (-link-). Amide and amine linkages are preferred. In the case of amide linkages, the linkages may be oriented so that material (B) is bonded directly either to the carbonyl or to the nitrogen of the amide linkage. These chemical moieties may be ionized. If so, it is understood in the art that many different counterions will serve to neutralize the charge of preparations of the chemical moiety. Suitable cations include, for example, $H^+$, $NH_4^+$ guanidinium, $Ag^+$, $Li^+$, $N^+$, $K^+$, $Mg^{2+}$, and $Mn^{2+}$. Suitable anions include, for example, halides, $OH^-$, carbonate, $SO_4^{2-}$, hexafluorophosphate and tetrafluoroborate.

It is also within the scope of this invention for the labeled substance (B) to be labeled by greater than one, e.g., two, three, four or more electrochemiluminescent centers.

Intermediates

The present invention also provides compounds that are particularly suitable as intermediates for attaching a luminescent europium-containing label to amino groups of chemical, biochemical and biological substances. These intermediates are thus particularly suitable for synthesizing chemical moieties according to the present invention. They include compounds having the formula

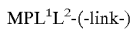

wherein M is a lanthanide element; P is a polydentate ligand of M; $L^1$ and $L^2$ are ligands of M, each of which may be a substance covalently bound to one or more of P, $L^1$, or $L^2$ through one or more covalent bond linkages, said linkages designated as (-link-) and being covalent bonds; P, $L^1$, and $L^2$ are of such number that the total number of bonds to M provided by the ligands of M equals the coordination number of M; and P, $L^1$, and $L^2$ are of such composition that the chemical moiety can be induced to emit electromagnetic radiation. In these compounds, (-link-) may contain activators such as N-hydroxysuccinimidyl moieties, amino moieties, or thiol moieties. Among the intermediates of the invention are the mono- and di-N-hydroxysuccinimide esters of europium 4,4'(dicarboxy)-2,2'-bipyridyl, bis(2,2'-bipyridyl) and their salts; and europium 4,4'(dichloromethyl)-2,2'-bipyridyl, bis(2,2'bipyridyl) and their salts.

A preferred method of synthesizing the europium-containing N-hydroxysuccinimide esters is to first react europium dichlorobis(2,2'-bipyridine) with 2,2'-bipyridine-4,4'-dicarboxylic acid in a hot aqueous methanol solution of sodium bicarbonate. After acidification, an aqueous solution of $NAPF_6$ is added to the solution of carboxylated europium compound. The isolated hexafluorophosphate salt of the europium complex is then esterified by reaction with N-hydroxysuccinimide in the presence of dicyclohexylcarbodiimide in dimethylformamide. Of course, many variations on the structure of the N-hydroxysuccinimide component are possible without substantially altering the usefulness of the inventive intermediates.

These intermediates may be ionized. If so, it is understood in the art that many different counterions will serve to neutralize the charge of preparations of the intermediate and form a salt. Suitable cations for forming these salts include for example $NH_4^+$, guanidinium, $Ag^+$, $Li^+$, $Na^+$, $K^-$, $Ca^{2+}$, $Mg^{2+}$, $Mn^{2+}$, and $Cd^{2+}$. Suitable anions for forming these salts include, for example, halides, carbonate, $SO_4^{2-}$ hexafluorophosphate, and tetrafluoroborate.

These intermediates are useful for labeling substances containing a free amino group capable of attacking the carboxylate ester, and thereby displacing N-hydroxysuccinimide, or of attacking the chloromethyl group, and thereby displacing chloride. Use of these intermediates to label analytes of interest is preferred over isothiocyanates of the prior art (e.g. Weber, U.S. Pat. No. 4,293,310). Isothiocyanates are generally prepared by reaction of a primary amine with carbon disulfide or thiophosgene, each of which is volatile and highly toxic. Carbon disulfide is also an acute fire and explosion hazard. The required precursor primary aromatic amines are more difficult to obtain than the precursor aromatic carboxylic acids used in the present invention. Also, the intermediates of the present invention are less reactive and more easily stored and handled than the isothiocyanate derivatives.

Determining the presence of chemical moieties: in general

The present invention provides methods for determining the presence of the chemical moieties of the invention by forming a reagent mixture which comprises the chemical moiety and detecting the presence of the moiety in such reagent mixture. As such throughout this application, and as will be readily appreciated by those skilled in the art to which this invention pertains, "reagent mixture" includes any and all combinations of the chemical moieties with other substances or reagents which may be employed in the practice of this invention. The specific combination may be in the form of an aqueous or nonaqueous solution, a suspension or emulsion, a solid or semisolid, or a gas, limited only by such limitations as may be imposed by the detection method used to detect the presence of the chemical moiety. For instance, electrochemiluminescence identifications may be performed with europium tris(1,1,1,2,2,3,3-heptafluoro-7,7-dimethyl-4,6-octanedionate) in aqueous solution and with terbium tris(2,2,6,6-tetramethyl-3,5-heptanedionate) in methyl chloride.

The chemical moieties may be detected by methods well known in the art including, for example, emission and absorption spectroscopy, e.g. ultraviolet absorption, infrared absorption, and fluorescence emissions; atomic absorption, electrochemical, e.g. anodic stripping voltametry; neutron activation and chemical methods. Of particular interest are photoluminescence, chemiluminescence and electrochemiluminescence methods. In one embodiment of the invention, the presence of the chemical moiety may be determined by inducing the chemical moiety to emit electromagnetic radiation and detecting the emitted radiation. In another embodiment of the invention, the chemical moiety may be induced to emit electromagnetic radiation by exposing the reagent mixture to electromagnetic, chemical or electrochemical energy. In yet another embodiment of the invention, the chemical moiety may be induced to emit electromagnetic radiation by exposing the reagent mixture to chemical or electrochemical energy.

Eu chelate may be determined at very low concentrations using luminescence techniques. Applicants' experience with Eu chelate labeled substances indicates the advantages of using europium-containing compounds as chemical labels. They are stable for long periods and may be attached efficiently to a wide variety of chemical, biochemical and biological materials. The labels are safe and relatively inexpensive. They give a highly characteristic signal and do not occur in nature. Measurements based on luminescence of the labels are sensitive, fast, reproducible and utilize simple instrumentation. There is very little interference with detection based on luminescence of these labels by such components as phosphate buffered saline, Tween (a surfactant), liver tissue extract or serum. Luminescence-based measurement of these labels does not destroy the sample or labeled materials and may be performed repetitively. The signal is generated repeatedly by each molecule of label, thereby enhancing the sensitivity with which the label may be detected. The presence of labeled materials may be determined qualitatively or quantitatively depending on the needs of the particular application. The word "determined", as used in this patent application, refers to either qualitative or quantitative determinations of the labeled material.

Accordingly, this invention provides a method of determining the presence of a chemical moiety having the formula:

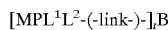

wherein M is europium; P is a polydentate ligand of M; $L^1$ and $L^2$ are ligands of M, each of which may be the same as, or different from each other ligand; B is a substance which is a ligand of M or is attached to one or more of P, $L^1$, or $L^2$; t is an integer equal to or greater than 1; (-link-) designates a covalent bond or bonds which connect B to P, $L^1$, or $L^2$; and P, $L^1$, $L^2$, $L^3$, $L^4$, $L^5$ and $L^6$ and B are of such composition and number that the chemical moiety can be induced to emit electromagnetic radiation and the total number of bonds to M provided by the ligands of M equals the coordination number of M.

The method comprises:

a) forming a reagent mixture under suitable conditions containing the chemical moiety;

b) inducing the moiety to emit electromagnetic radiation by exposing the reagent mixture to chemical energy or electrochemical energy; and c) detecting the emitted electromagnetic radiation and thereby determining the presence of the chemical moiety.

Suitable conditions for forming the reagent mixture will be known to those skilled in the art and will depend on the type of reagent mixture involved. For example, suitable conditions for an aqueous reagent mixture may include appropriate concentrations of chemical moiety and other reagents such as oxidants, pH, salt concentration and the like. For a solid sample, suitable conditions for forming a reagent mixture may include addition of a conducting liquid.

Determining the presence of bound chemical moieties

The methods of this invention include a method of determining the chemical moiety wherein the moiety is capable of binding to a chemical agent, i.e. forming a specific complex with the chemical agent.

Suitable chemical agents include, but are not limited to, whole cells, viruses, subcellular particles, nucleic acids polysaccharides, proteins, glycoproteins, lipoproteins, lipopolysaccharides, lipids, fatty acids, peptides cellular metabolites, hormones, pharmacological agents, tranquilizers, barbiturates, alkaloids, steroids, vitamins, amino acids, sugars or non-biological polymers.

In one embodiment of the invention, the chemical agent may be immobilized on the surface of an assay vessel. In another embodiment, the chemical agent may be a serum-derived antibody or a monoclonal antibody.

Of particular interest are antibody-antigen pairs of materials. This binding method may be used to determine the presence of labeled antigens, such as, for example, digoxin or digitoxin in complex mixtures by first exposing the mixture to immobilized antibodies specific for the antigen of interest, and then measuring the amount of labeled material bound to the immobilized antibodies.

The invention further provides methods for determining the presence of analytes of interest which bind to a chemical moiety, said moiety having the formula:

$$[MPL^1L^2\text{-(-link-)-}]_tB$$

wherein M is europium; P is a polydentate ligand of M; $L^1$ and $L^2$ are ligands of M, each of which may be the same as, or different from each other ligand; B is a substance which is a ligand of M or is attached to one or more of P, $L^1$, or $L^2$; t is an integer equal to or greater than 1; (-link-) designates a covalent bond or bonds which connect B to P, $L^1$, or $L^2$; and P, $L^1$, $L^2$, $L^3$, $L^4$, $L^5$ and $L^6$ and B are of such composition and number that the chemical moiety can be induced to emit electromagnetic radiation and the total number of bonds to M provided by the ligands of M equals the coordination number of M.

The method comprises:
a) forming a reagent mixture under suitable conditions containing the chemical moiety;
b) inducing the moiety to emit electromagnetic radiation by exposing the reagent mixture to chemical energy or electrochemical energy; and
c) detecting the emitted electromagnetic radiation and thereby determining the analyte of interest.

Within this application "complementary material" means any substance capable of forming complexes with both an analyte of interest and a labeled analyte of interest or a labeled analogue of an analyte of interest.

Electromagnetic radiation

The phrase "inducing to emit electromagnetic radiation" refers to creating an excited states of said moiety which luminesces at wavelengths between 200 nanometers and 900 nanometers at ambient temperatures. The present invention envisions lanthanide-containing moieties such as europium-containing moieties and encompasses the wide variety of luminescent moieties which can be made by varying the chemical structure of the ligands. Each of these variations in the metal and the ligands can change the precise value of the energy input required to create the luminescent excited state. Similarly, the wavelength of the emitted electromagnetic radiation will be dependent upon the nature and environment of the europium-containing material. Generally, photoluminescence excitation and emission will occur with electromagnetic radiation of between about 200 nanometers and about 900 nanometers in wavelength. Chemiluminescent and electrochemiluminescent emission will generally occur with the emitted electromagnetic radiation being between about 100 nanometers and about 1500 nanometers in wavelength, and preferably of wavelengths between 200 and 900 nanometers. The potential at which the reduction or oxidation of the chemical moiety will occur depends upon its exact chemical structure as well as factors such as the pH of the solution and the nature of the electrode used. Generally, it is well known in the art how to determine the optimal emission and excitation wavelengths in a photoluminescent system, and the optimal potential and emission wavelength of an electrochemiluminescent and chemiluminescent system.

It should be clear that there are many methods for quantifying the amount of luminescent species present. The rate of energy input into the system can provide a measure of the luminescent species. Suitable measurements include, for example, measurements of electric current when the luminescent species is generated electrochemically, the rate of reductant or oxidant utilization when the luminescent species is generated chemically or the absorption of electromagnetic energy in photoluminescent techniques. In addition, of course, the luminescent species can be detected by measuring the emitted electromagnetic radiation. All of these measurements can be made either as continuous, rate-based measurements, or as cumulative methods which accumulate the signal over a long period of time. An example of rate-based measurements is the use of photomultiplier tubes, photodiodes or phototransistors to produce electric currents proportional in magnitude to the incident light intensity. Examples of cumulative methods are the integration of rate-based data, and the use of photographic film to provide cumulative data directly.

All of these luminescence-based methods entail repeated luminescence by the europium-containing compound. The repetitive nature of the detectable event distinguishes these labels from radioactive isotopes or bound chemiluminescent molecules such a luminal. The latter labels produce a detectable event only once per molecular (or atom) of label, thereby limiting their detectability.

Binding methods

In the chemical moieties useful in these methods, biological and nonbiological substance (B) may be incorporated into the moieties by coordination directly to M or by attachment to a ligand of M. Attachment may be through covalent bonding, or by electrostatic or hydrogen bonding. Many diverse means of effecting covalent bonding of substances (B) to ligands of M are available. The attaching linkage may be, for example, an amide or amine bond, an ester or thioester, an ether or thioester, or any of many other means known to the art. The type of linkage will be determined by the substituents of the ligand and the suitable chemical groups available for binding with the ligand on the substance that is to be labeled.

The analyte of interest and the chemical moiety may be any pair of substances which are capable of binding together in a specific manner. Such substances include for example, whole cells, viruses, subcellular particles, nucleic acids, polysaccharides, proteins, glycoproteins, lipoproteins, lipopolysaccharides, lipids, fatty acids, peptides, cellular metabolites, hormones, pharmacological agents, tranquilizers, barbiturates, alkaloids, steroids, vitamins, amino acids, sugars and non-biological polymers. Of particular interest are antibody-antigen pairs. One embodiment of the invention provides the use of labeled antibodies to determine the presence of cell surface antigens, or to label particular cells for detection by cell sorting methods. Antigens immobilized by, for example, attachment to immobilized, unlabeled antibodies can be detected by labeled antibodies in a method commonly known as a "sandwich" method.

In competitive binding assays, B may be the same substance as the analyte of interest or an analogue of the analyte, and capable of participating in the formation of a specific complex with a complementary material. Such analytes and complementary materials include, whole cells, viruses, subcellular particles, nucleic acids, polysaccharides, proteins, glycoproteins, lipoproteins, lipopolysaccharides, lipids, fatty acids, peptides, cellular metabolites, hormones, pharmacological agents, tranquilizers, barbiturates, alkaloids, steroids, vitamins, amino acids, sugars and non-biological polymers. Examples of such analytes and complementary materials include insulin, digoxin, digitoxin, T4 thyroid hormone, a fungus or nematode, a serum-derived antibody or a monoclonal antibody, a DNA fragment or an RNA fragment of particular interest are antibody-antigen based methods. These methods "are analogous to the well known radioimmunoassay, wherein an analyte of interest is detected when it displaces a radioactive analogue of the analyte from an antibody. The marry variations on radioimmunoassay known to the art can, in principle, be used to advantage by employing moieties labeled according to the present invention in place of radioactively labeled compounds.

The present invention further provides heterogeneous and homogeneous binding methods which utilize the chemical moieties provided herein. In heterogeneous binding methods, the bound labeled substance must be physically separated from the unbound labeled substance before measurement of the presence of label. This is frequently accomplished in antibody-antigen systems by immobilizing one component, the antibody for example, by attachment to an insoluble matrix such as a filter or to the surface of beads or reaction vessels such as test tubes. The antigen-containing solution is poured through the filter or into the reaction vessel, and then washed away from the filter or sides of the reaction vessel. Only antigen specifically bound to antibody will remain to be determined.

In homogeneous methods, by contract, the bound and unbound labeled material are present in the same reaction mixture when the presence of label is measured. This is possible when binding modifies the properties of the signal detectable from the label. There are many ways that luminescent labels can be used in homogeneous systems. For example, binding of the analyte to the chemical moiety can directly influence the signal detectable from the label. Additionally, a luminescence quencher may be positioned on an antibody so that binding of a labeled antigen to the antibody could result in suppression of the luminescence of the label by the luminescence quencher on the antibody. Many homogeneous methods for luminescent labels are known to the art; and some of them are reviewed in Boguslaski and Li (1982), "Homogeneous Immunoassays," *Applied Biochemistry and Biotechnology*, 7, pp. 401–414.

In one embodiment of the invention, the analyte is fixed to an insoluble matrix. Such a method may be performed as a sandwich assay i.e. the chemical moiety becomes bound to the immobilized analyte and unbound moiety is washed away from the matrix.

Another embodiment comprises a chemical agent to which the moiety is capable of binding being fixed to an insoluble matrix and the chemical moiety being a component of a biological fluid or synthetic reaction.

Additionally, the competitive binding methods of the present invention may comprise the complementary material being fixed to an insoluble matrix.

Both the heterogeneous and homogeneous competitive methods of the present invention comprise the complementary material being monoclonal antibody and the insoluble matrix being the surface of an assay vessel.

Inducing the emission of electromagnetic radiation

The methods of the present invention may be performed by exposing the reagent mixture to electrochemical energy or to chemical energy. Additionally, the reagent mixture may be exposed to a combination of electromagnetic radiation, chemical energy, and electrochemical energy.

The chemical moiety may be oxidized by exposure to an energy source. Such an energy source amy be a chemical oxidizing agent. Examples of such oxidizing agents include CE(IV) salts or $PbO_2$. Furthermore, the chemical moiety may be reduced by exposure to an energy source. Such an energy source may be a chemical reducing agent. An example of a suitable reducing agent is magnesium.

The methods of the present invention may comprise inducing the chemical moieties to emit electromagnetic radiation more than once.

The reagent mixture may comprise oxalate, pyruvate, lactate, malonate, citrate, tartrate or peroxydisulfate. Furthermore, the chemical moiety may be reduced by exposure to an energy source and the reagent mixture may comprise peroxydisulfate. Moreover, the chemical moiety may be oxidized by exposure to an energy source and the reagent mixture may comprise oxalate, pyruvate, lactate, malonate, citrate or tartrate.

Methods of detecting the chemical moiety are provided wherein the reagent mixture is continuously exposed to electrode whose potential oscillates between a potential sufficient to effect the reduction of said chemical moiety and a potential sufficient to effect the oxidation of the chemical moiety.

The chemical moiety may be oxidized by exposure to an electrode whose potential oscillates above and below a potential sufficient to oxidize the chemical moiety, the reagent mixture comprising oxalate, pyruvate, lactate, malonate, tartrate or citrate. Moreover, the chemical moiety may be oxidized by exposure to an electrode whose potential is constant and sufficient to oxidize it, the reagent mixture comprising oxalate, pyruvate, lactate, malonate, tartrate or citrate.

The chemical moiety may also be reduced by exposure to an electrode whose potential oscillates above and below a potential sufficient to reduce it, the reagent mixture comprising peroxydisulfate. Such reagent mixture may additionally comprise acetonitrile. Furthermore, the chemical moiety may be reduced by exposure to an electrode whose potential is constant and sufficient to reduce it, the reagent mixture comprising peroxydisulfate. Such reagent mixture may also comprise acetonitrile.

When the chemical moiety is exposed to electrochemical or chemical energy, the emitted electromagnetic radiation may be continuously detected. Such electromagnetic radiation may be detected visually or with a photodiode. Furthermore, when the chemical moiety is exposed to electrochemical or chemical energy, the emitted radiation may be detected cumulatively, e.g. with a photographic film.

U.S. Pat. No. 5,147,806 (Kamin et al.) discloses a method and apparatus for conducting electrochemiluminescence measurements. The method and apparatus control the initial conditions relating to the surface state of a triggering working electrode by reproducibly creating and maintaining a favorable surface condition. This enhances the precision and detection limit of the measurements. Assays are performed with electrochemiluminescence detection in a flow-through cell environment. The precision and detection limit are enhanced by alternating initialization and measurement steps. The tire disclosure of the Kamin et al. patent is expressly corporated herein by reference.

Means and systems

The present invention also provides a system for determining the presence of a chemical moiety having the formula:

[MPL¹L²-(-link-)-]ₜB wherein M is europium; P is a polydentate ligand of M; $L^1$ and $L_2$ are ligands of M, each of which may be the same as, or different from each other ligand; B is a substance which is a ligand of M or is attached to one or more of P, $L^1$, or $L^2$; t is an integer equal to or greater than 1; and P, $L^1$, $L^2$, $L^3$, $L^4$, $L^5$ and $L^6$ and B are of such composition and number that the chemical moiety can be induced to emit electromagnetic radiation and the total number of bonds to M provided by the ligands of M equals the coordination number of M.

The system comprises:
a) a reagent mixture comprising the chemical moiety;
b) means for inducing the chemical moiety to emit electromagnetic radiation; and
c) means for detecting the emitted electromagnetic radiation.

A system for determining the presence of an analyte of interest which binds to a chemical moiety is also provided, wherein the moiety having the structural formula:

[MPL¹L²-(-link-)-]ₜB is used, with the components of the structure being the same as those described above. This system comprises:
a) the chemical moiety;
b) a means for contact the chemical moiety with the analyte of interest to form a reagent mixture;
c) a means for inducing the chemical moiety to emit electromagnetic radiation; and
d) a means for detecting the emitted electromagnetic radiation.

Electromagnetic radiation of differing wavelengths

This invention also concerns compositions which comprise the europium-containing chemical moieties of this invention and one or more different chemical moieties each of which can be induced to emit electromagnetic radiation of a different distinct wavelength. These compositions are useful in methods and systems of detecting two or more different substances or analytes of interest contained in a mixture of the same and other substances.

In one embodiment of the inventions the chemical moieties are each attached to different analytes of interest.

The different chemical moiety or moieties may be any suitable chemical moiety such as inorganic, organic or organometallic compounds which can be induced to emit electromagnetic radiation, e.g. rubrene or 9,10-diphenylanthracene. These moieties may be such moieties that are induced to emit electromagnetic radiation when exposed to energy of different values or sources than the energy used to induce electromagnetic radiation from the europium-containing chemical moieties. In a specific embodiment of the invention, each other chemical moiety emits electromagnetic radiation of a different distinct wavelength when induced to emit electromagnetic radiation by energy of the same source and value that induces the europium-containing chemical moiety to emit electromagnetic radiation.

Methods for determining these chemical moieties comprise forming a reagent mixture under suitable conditions containing the chemical moieties and then inducing the chemical moieties to emit electromagnetic radiation by exposing the reagent mixture to chemical energy or electrochemical energy. The presence of each of the moieties is determined by detecting the electromagnetic radiation of different wavelengths emitted by each of the moieties.

The invention also concerns a method of determining the presence of one or more analytes of interest which bind selectively to different chemical moieties present in the same mixture. The method comprises contacting the analytes with the chemical moieties under suitable conditions so as to form a reagent mixture. The moieties are induced to emit electromagnetic radiation by exposing the reagent mixture to chemical energy or electrochemical energy and the emitted electromagnetic radiation of different wavelengths is detected to determine the presence of each of the analytes of interest.

These methods in which the presence of two or more chemical moieties is determined in a mixture are applicable to all instances described previously for determining the europium-containing luminescent labels. This embodiment, however, allows for the determination of two or more different substances present in the same sample simultaneously.

Also provided are systems for determining the presence of one or more different chemical moieties or analytes of interest which bind to the chemical moieties, each of which may be induced to emit electromagnetic radiation of a different wavelength. In one embodiment of the invention, each moiety is attached to a different analyte of interest.

EXAMPLES

This invention is illustrated in the examples which follow. The examples are set forth to aid in an understanding of the invention but are not intended to, and should not be construed to, limit in any way the invention as set forth in the claims which follow thereafter.

Example 1

Tris(6,6,7,7,8,8,8-heptofluoro-2,2-dimethyl-3,5-octanedionato)europium

The sodium salt of 2,2-dimethyl-6,6,7,7,8,8,8-heptafluoro-3,5-octanedione was prepared as a white precipitate by the addition of 0.1M aqueous NaOH (0.7 ml, 0.7 mmol) to 2,2-dimethyl-6,6,7,7,8,8,8-heptafluoro-3,5-octanedione (208 mg, 0.7 mmol) to form a solution containing the ligand. Absolute ethanol (0.7 ml) was then added with stirring and the solution was warmed to 40° C. for 15 minutes to effect complete dissolution of the salt. Eu(NO₃)₃ (100 mg, 0.23 mmol) dissolved in a 1:1 water/ethanol mixture (1.0 ml) was added to the ligand solution in one portion. A yellow oil formed immediately. The mixture was stirred at room temperature for one hour. After this time, water (15 ml) was added and the product was extracted with methylene chloride (20 ml) and dried over anhydrous sodium sulfate. The solvent was then removed under vacuum to afford 220 mg of tris(6,7,7,8,8,8-heptofluoro-2,2-dimethyl-3,5-octane-dionato)europium as an oil (92% of theoretical yield). FAB mass spectrometry results were as follows: m/e, 1077/1075 (M⁺+K), 1061/1059 (M⁺+Na), 1039/1037 (M⁺+1). The product showed identical properties (mass spectrometry, tlc) to the commercial compound available from Aldrich (Cat. No. 16,039–8, CAS No. 17631–68–4).

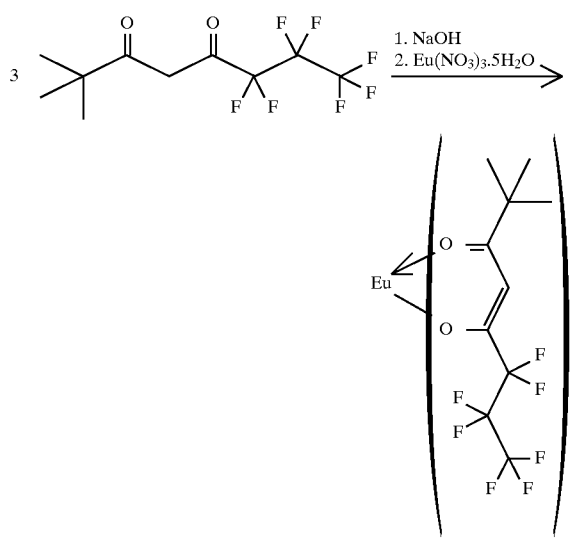

Example 2
Effect of TPA on Electrochemiluminescence of Eu*

Figure 1B:
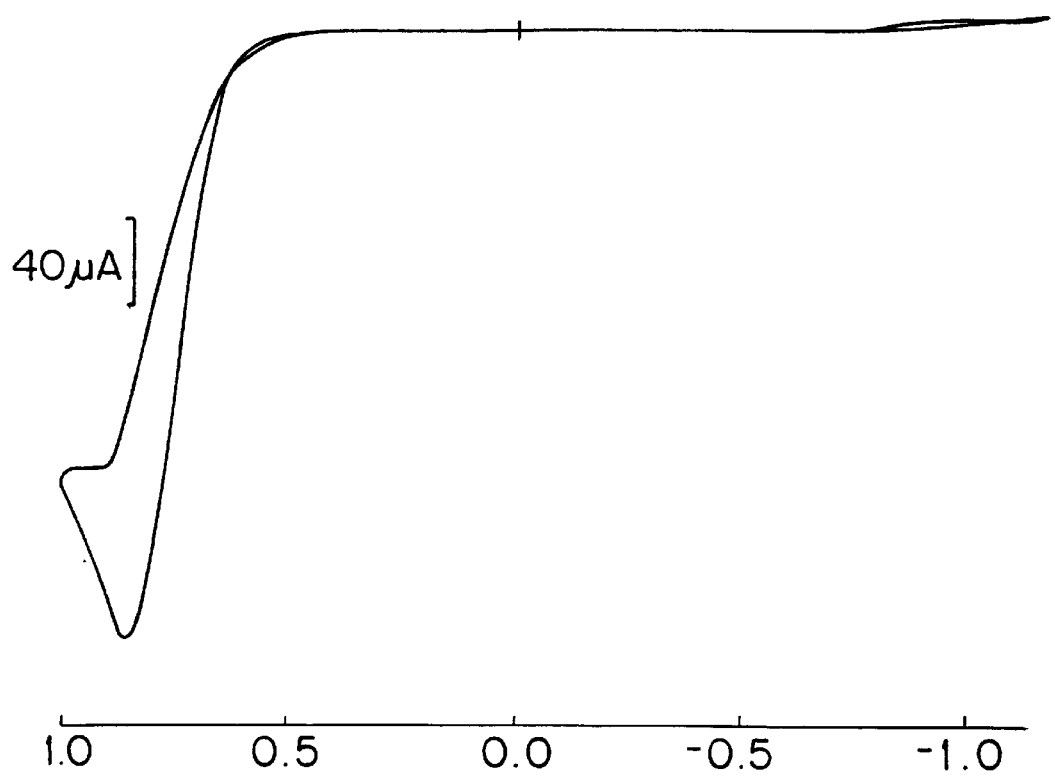
FIG. 1(b) shows a cyclic voltammogram for 2 mM europium chelate with 10 mM tripropylamine (hereinafter "TPA") added in 0.1M TBAPF$_6$ acetonitrile solution.

Cyclic voltammograms were established for 2 mM europium chelate in 0.1M TBAPF$_6$ acetonitrile solution and for 2 mM europium chelate with 10 mM TPA added in 0.1M TBAPF$_6$ acetonitrile solution. Both voltammograms were established with a glassy carbon electrode (θ=3 mm) at a scan rate of 0.1 Volts/second. The results are depicted, respectively, in FIGS. 1(a) and 1(b). The results confirm that the electrochemiluminescence of Eu* is directly caused by the oxidation of TPA.

Example 3
N-Hydroxysuccinimide ester activator

An electrochemiluminescent rare earth chelate linker containing an N-hydroxysuccinimide ("NHS") ester can be made by forming europium bis(1,1,1,2,2,2,3,3-heptafluoro-7,7-dimethyl-4,6-octanedionate) and separately synthesizing the key linking ligand, N-hydroxysuccinimidyl-9,9,10,10,11,11,11-heptafluoro-6,8-undecanoate. Reacting these two products together under basic conditions affords the desired europium bis(1,1,1,2,2,2,3,3-heptafluoro-7,7-dimethyl-4,6-octanedionate) (N-hydroxysuccinimidyl-9,9,10,10,11,11,11-heptafluoro-6,8-undecanoate). This reaction, which is depicted below, is possible since the rate of formation of the europium complexes is much faster than the rate of NHS ester hydrolysis at pH 8–9.

NHS ester complexes are used to effect linkages to melecules, biomolecules, and biopolymers of intereset that either naturally contain primary or secondary amine functions or that have been modified to containe such amines.

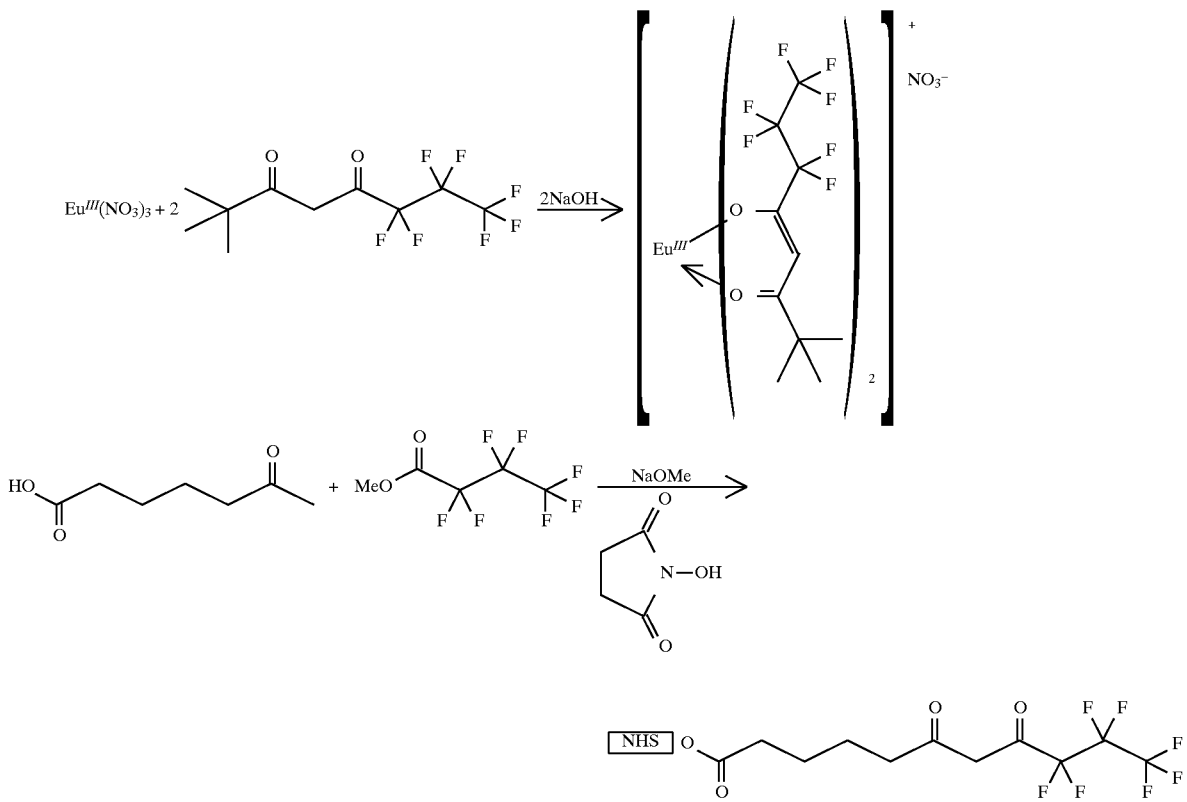

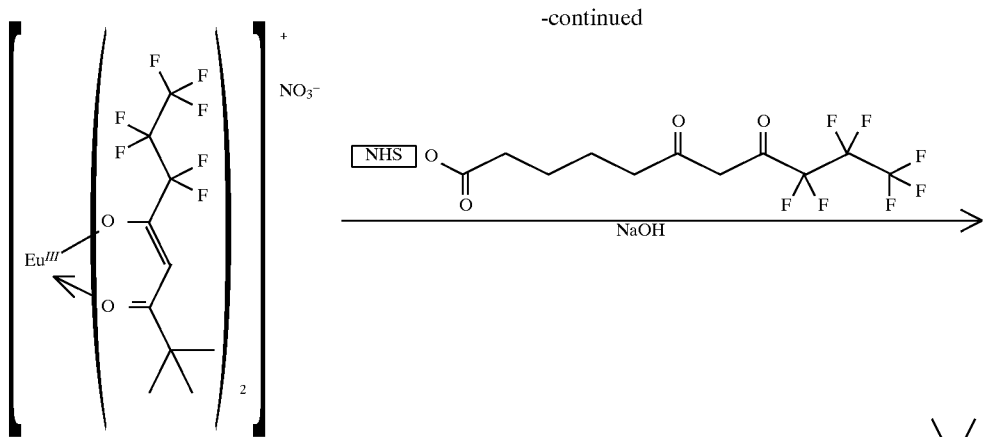
Example 4
N-Hydroxysuccinimide ester activator
Alternatively, an electrochemiluminescent rare earth chelate linker containing an NHS ester can be made by an alternate route, depicted below, in which the NHS ester is formed after the third ligand has been complexed to the europium.
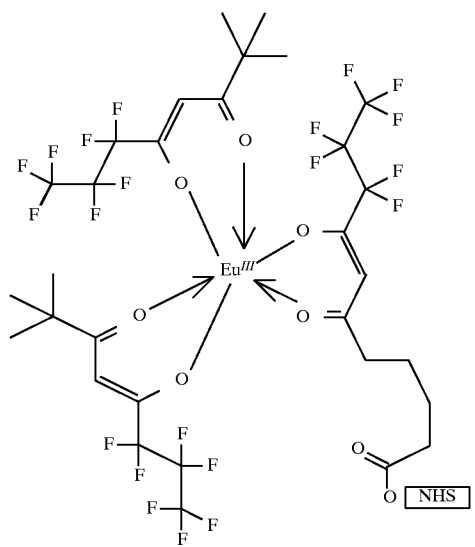
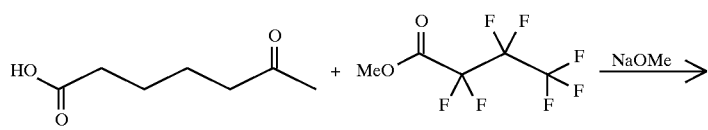
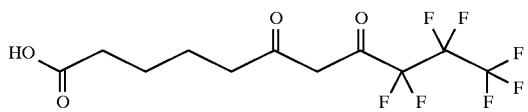

-continued
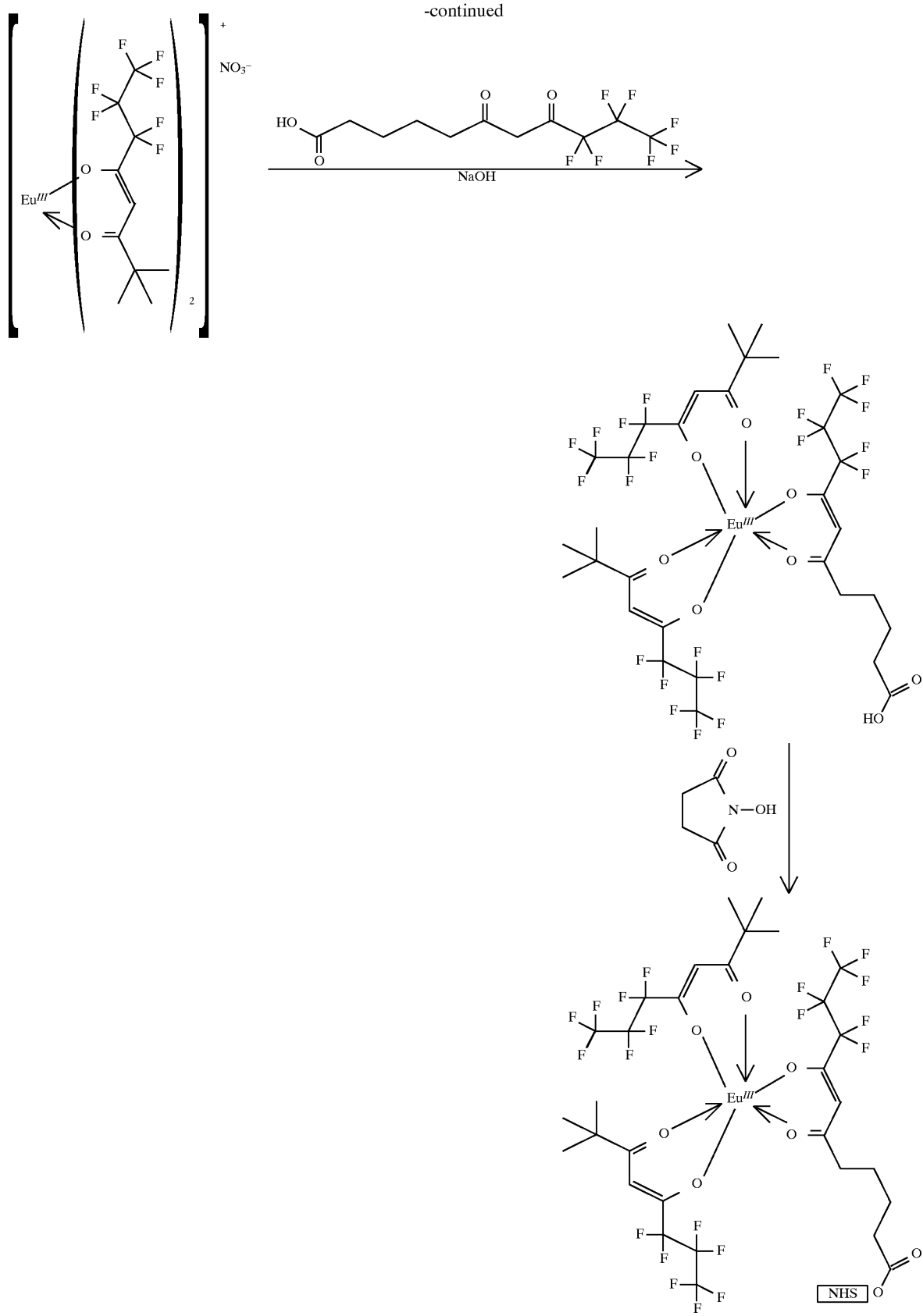

Example 5

Dicyclohexylcarbodiimide activator

An electrochemiluminescent rare earth chelate linker containing a dicyclohexylcarbodiimide in place of the NHS ester can be made by both the procedure of Example 3 and the alternative procedure of Example 4.

Dicyclohexylcarbodiimide complexes are used to effect linkages to melecules, biomolecules, and biopolymers of intereset that either naturally contain primary or secondary amine functions or that have been modified to containe such amines.

Example 6

Amine activator

An example of an amine ligand, for linking to electrophilic acyl centers such as NHS esters to form amides or to Michael-type acceptors such as maleimides, is depicted below.

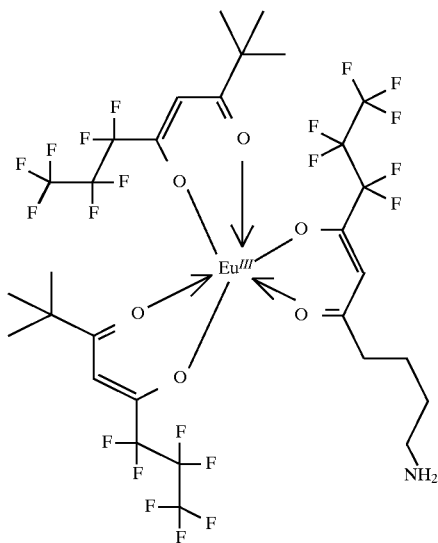

Example 7

Thiol activator

An example of a thiol linker, for linking to other thiols, forming thioethers with electrophilic alkyl species such as alkyl bromides, or reacting with Michael-type acceptors such as maleimides, is depicted below.

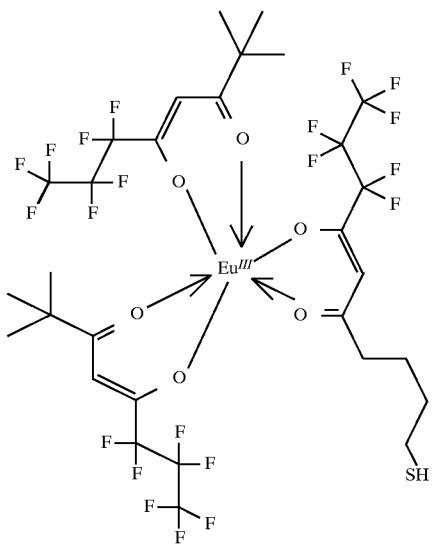

Example 8

Labelling of bovine serum albumin with activated europium complex

Europium bis(1, 1, 1,2,2,2,3,3-heptafluoro-7,7-dimethyl-4,6-octanedionate) (N-hydroxysuccinimidyl-9,9,10,10,11, 11,11-heptafluoro-6,8-undecanoate) in dimethylformamide solution is added to a stirred solution of bovine serum albumin (BSA) in aqueous Physiol ogic Buffered Saline (PBS, 5 ml; 25 mg/ml BSA). The mixture is stirred overnight, and precipitate is removed by centrifugation. The supernatant contains europium-labelled BSA.

Example 9

Labelling of human immunoglobulin G with activated europium complex

Europium bis(1, 1, 1,2,2,2,3,3-heptafluoro-7,7-dimethyl-30 4,6 -octanedionate) (N-hydroxysuccinimidyl-9, 9,10,10,11,11,11-heptafluoro-6,8-undecanoate) in dimethylformamide solution is added to a stirred solution of human immunoglobulin G (IgG) in aqueous buffer. The europium-labelled IgG solution fluoresces brightly after extensive dialysis, indicating that the europium complex is bound to the high molecular weight affinity-purified human IgG.

Although the present invention has been described and illustrated with reference to certain preferred and other specific embodiments thereof, those skilled in the art will be apprised by the teachings herein of principles of wide applicability. The invention patented, therefore, is determined only by the scope and spirit of the appended claims.

What is claimed is:

1. A method of determining the presence of a chemical moiety, said chemical moiety having the formula

[MPL$^1$L$^2$-(-link-)-]$_t$B 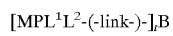

wherein M is a lanthanide;

P is a polydentate ligand of M;

L$^1$ and L$^2$ are ligands of M, each of which may be a substance covalently bound to one or more of P, L$^1$ or L$^2$ through one or more covalent bond linkages, said linkages designated as (-link-) and being covalent bonds linking B with at least one of P, L$^1$ or L$^2$;

t is an integer equal to or greater than 1;

B is a biological substance, a synthetic substance which is capable of competing with a biological substance in a competitive binding reaction with a complementary material, or a non-biological substance;

P, $L^1$ or $L^2$, and B are of such number that the total number of bonds to M provided by the ligands of M equals the coordination number of m; and P, $L^1$ or $L^2$, and B are of such composition that the chemical moiety can be induced to repeatedly emit electromagnetic radiation;

which method comprises (a) forming a reagent mixture containing the chemical moiety, or the chemical moiety and an agent which upon exposure of the reagent mixture to electrochemical energy forms either a reductant or an oxidant;

(b) exposing the reagent to electrochemical energy the potential of which oscillates between a potential sufficiently positive to oxidize the chemical moiety and a potential sufficiently negative to reduce the chemical moiety, or to electrochemical energy such that said chemical moiety is oxidized and the agent forms a reductant, or such that said chemical moiety is reduced and the agent forms an oxidant, thereby to induce the chemical moiety to repeatedly electrochemiluminescence; and (c) detecting emitted luminescence thereby to determine the presence of the chemical moiety.

2. The method of claim 1, wherein B is a member selected from the group consisting of whole cells, subcellular particles, polypeptides, proteins, nucleic acids, polysaccharides alkaloids, steroids, vitamins, amino acids, plant pathogens, serum-derived antibodies, monoclonal antibodies, and T4 thyroid hormones.

3. The method of claim 1, wherein (-link-) is the linkage formed between one of said ligands and a free amino group which is part of B.

4. The method of claim 1, wherein (-link-) is the linkage formed between a carboxyl group and a free amino group which is part of B.

5. The method claim 1, wherein M is europium or terbium and (-link-) is an amide linkage that covalently bonds B with a substituted bipyridyl ligand, the amide linkage being formed by reaction of a carboxyl substituent on said substituted bipyridyl ligand with a free amino group which is part of B.

6. The method of claim 1, wherein M is europium and P, $L^1$, and $L^2$ are each 6,6,7,7,8,8,8-heptafluoro-2,2-dimethyl-3,5-octanedionato ligands.

7. The method of claim 1, wherein M is terbium and P, $L^1$, and $L^2$ are each 2,2,6,6-tetramethyl-3,5-heptane-dionato ligands.

8. The method of claim 1, wherein M is europium;

P, $L^1$, and $L^2$, each is a semi-aromatic oxygen-containing ligand, each of said ligands being the same or not the same as each other ligand; and (-link-) is one or more amide linkages, ester or thioester linkages, or ether or thioether linkages, each said linkage covalently bonding B with at least one of P, $L^1$, and $L^2$.

9. A method of determining the presence of an analyte of interest which binds to a chemical moiety, which comprises (a) forming a reagent mixture comprising the chemical moiety, or comprising the chemical moiety and an agent which upon exposure of the reagent mixture to electrochemical energy forms either a reductant or an oxidant, and the analyte of interest; such that the chemical moiety and the analyte specifically bind to one another, said chemical moiety having the formula

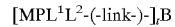

[MPL$^1$L$^2$-(-link-)-]$_t$B wherein M is a lanthanide;

P is a polydentate ligand of M;

$L^1$ and $L^2$ are ligands of M, each of which may be a substance covalently bound to one or more of P, $L^1$, or $L^2$ through one or more covalent bond linkages, said linkages designated as (-link-) and being covalent bonds linking B with at least one of P, $L^1$ or $L^2$;

t is an integer equal to or greater than 1;

B is a biological substance, a synthetic substance which is capable of competing with a biological substance in a competitive binding reaction with a complementary material, said biological substance or synthetic substance being capable of specifically binding to the analyte of interest;

P, $L^1$, $L^2$, and B are of such number that the total number of bonds to M provided by the ligands of M equals the coordination number of M; and P, $L^1$, $L^2$, and B are of such composition that the chemical moiety can be induced to repeatedly emit electromagnetic radiation;

(b) exposing the reagent mixture to electrochemical energy the potential of which oscillates between a potential sufficiently positive to oxidize the chemical moiety and a potential sufficiently negative to reduce the chemical moiety, or to electrochemical energy such that said chemical moiety is oxidized and the agent forms a reductant, or such that said chemical moiety is reduced and the agent forms an oxidant, thereby to induce the chemical moiety to repeatedly electrochemiluminesce; and (c) detecting emitted luminescence thereby to determine the presence of the analyte of interest.

10. A competitive binding method of determining the presence of an analyte of interest wherein the analyte and a chemical moiety bind competitively to a complementary material, which comprises (a) forming a reagent mixture comprising the analyte of interest, the complementary material and the chemical moiety, or the chemical moiety and an agent which upon exposure of the reagent mixture to electrochemical energy forms either a reductant or an oxidant, such that the chemical moiety and the analyte of interest bind competitively to the complementary material; said chemical moiety having the formula

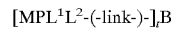

[MPL$^1$L$^2$-(-link-)-]$_t$B wherein M is a lanthanide;

P is a polydentate ligand of M;

$L^1$ and $L^2$ are ligands of M, each of which may be a substance covalently bound to one or more of P, $L^1$, or $L^2$ through one or more covalent bond linkages, said linkages designated as (-link-) and being covalent bonds linking B with at least one of P, $L^1$, or $L^2$;

t is an integer equal to or greater than 1;

B is a biological substance or a synthetic substance which is capable of competing with a biological substance in a competitive binding reaction with a complementary material, said biological substance or synthetic substance being capable of binding to the complementary material;

P, $L^1$, $L^2$, and B are of such number that the total number of bonds to M provided by the ligands of M equals the coordination number of M; and P, $L^1$, $L^2$, and B are of such composition that the chemical moiety can be induced to repeatedly emit electromagnetic radiation;

(b) exposing the reagent mixture to electrochemical energy the potential of which oscillates between a potential sufficiently positive to oxidize the chemical moiety and a potential sufficiently negative to reduce the chemical moiety, or to electrochemical energy such that said chemical moiety is oxidized and the agent forms a reductant, or such that said chemical moiety is reduced and the agent forms an oxidant, thereby to induce the chemical moiety to repeatedly electrochemiluminesce; and (c) detecting emitted luminescence thereby to determine the presence of the analyte of interest.

11. A method of determining the presence of a chemical moiety, said chemical moiety having the formula $$[MPL^1L^2\text{-(-link-)-}]_tB$$

wherein M is a lanthanide;

P is a polydentate ligand of M;

$L^1$ and $L^2$ are ligands of M, each of which may be a substance covalently bound to one or more of P, $L^1$ or $L^2$ through one or more covalent bond linkages, said linkages designated as (-link-) and being covalent bonds linking B with at least one of P, $L^1$ or $L^2$;

t is an integer equal to or greater than 1;

B is a biological substance, a synthetic substance which is capable of competing with a biological substance in a competitive binding reaction with a complementary material, or a non-biological substance;

P, $L^1$ or $L^2$, and B are of such number that the total number of bonds to M provided by the ligands of M equals the coordination number of m; and P, $L^1$ or $L^2$, and B are of such composition that the chemical moiety can be induced to repeatedly emit electromagnetic radiation;

which method comprises:

(a) forming a reagent mixture containing the chemical moiety;

(b) exposing the reagent mixture to electrochemical energy the potential of which oscillates between a potential sufficiently positive to oxidize the chemical moiety and a potential sufficiently negative to reduce the chemical moiety, thereby to induce the chemical moiety to repeatedly electrochemiluminesce; and (c) detecting emitted luminescence thereby to determine the presence of the chemical moiety.

12. A method of determining the presence of a chemical moiety, said chemical moiety having the formula $$[MPL^1L^2\text{-(-link-)-}]_tB$$

wherein M is a lanthanide;

P is a polydentate ligand of M;

$L^1$ and $L^2$ are ligands of M, each of which may be a substance covalently bound to one or more of P, $L^1$ or $L^2$ through one or more covalent bond linkages, said linkages designated as (-link-) and being covalent bonds linking B with at least one of P, $L^1$ or $L^2$;

t is an integer equal to or greater than 1;

B is a biological substance, a synthetic substance which is capable of competing with a biological substance in a competitive binding reaction with a complementary material, or a non-biological substance;

P, $L^1$ or $L^2$, and B are of such number that the total number of bonds to M provided by the ligands of M equals the coordination number of m; and P, $L^1$ or $L^2$, and B are of such composition that the chemical moiety can be induced to repeatedly emit electromagnetic radiation;

which method comprises:

(a) forming a reagent mixture containing the chemical moiety and an agent which upon exposure of the reagent mixture to electrochemical energy forms a reductant;

(b) exposing the reagent mixture to electrochemical energy such that said chemical moiety is oxidized and the agent forms a reductant, thereby to induce the chemical moiety to repeatedly electrochemiluminesce; and (c) detecting emitted luminescence thereby to determine the presence of the chemical moiety.

13. A method of determining the presence of a chemical moiety, said chemical moiety having the formula $$[MPL^1L^2\text{-(-link-)-}]_tB$$

wherein M is a lanthanide;

P is a polydentate ligand of M;

$L^1$ and $L^2$ are ligands of M, each of which may be a substance covalently bound to one or more of P, $L^1$ or $L^2$ through one or more covalent bond linkages, said linkages designated as (-link-) and being covalent bonds linking B with at least one of P, $L^1$ or $L^2$;

t is an integer equal to or greater than 1;

B is a biological substance, a synthetic substance which is capable of competing with a biological substance in a competitive binding reaction with a complementary material or a non-biological substance;

P, $L^1$ or $L^2$, and B are of such number that the total number of bonds to M provided by the ligands of M equals the coordination number of m; and P, $L^1$ or $L^2$, and B are of such composition that the chemical moiety can be induced to repeatedly emit electromagnetic radiation;

which method comprises:

(a) forming a reagent mixture containing the chemical moiety and an agent which upon exposure of the reagent mixture to electrochemical energy forms an oxidant;

(b) exposing the reagent mixture to electrochemical energy such that said chemical moiety is reduced and said agent forms an oxidant, thereby to induce said chemical moiety to repeatedly electrochemiluminescence; and (c) detecting emitted luminescence thereby to determine the presence of the chemical moiety.

14. A method of determining the presence of a chemical moiety, said chemical moiety having the formula $$[MPL^1L^2\text{-(-link-)-}]_tB$$

wherein M is a lanthanide;

P is a polydentate ligand of M;

$L^1$ and $L^2$ are ligands of M, each of which may be a substance covalently bound to one or more of P, $L^1$ or $L^2$ through one or more covalent bond linkages , said linkages designated as (-link-) and being covalent bonds linking B with at least one of P, $L^1$ or $L^2$;

t is an integer equal to or greater than 1;

B is a biological substance, a synthetic substance which is capable of competing with a biological substance in a competitive binding reaction with a complementary material, or a non-biological substance;

P, $L^1$ or $L^2$, and B are of such number that the total number of bonds to M provided by the ligands of M equals the coordination number of m; and P, $L^1$ or $L^2$, and B are of such composition that the chemical moiety can be induced to repeatedly emit electromagnetic radiation;

which method comprises:

(a) forming an assay reagent mixture containing the chemical moiety and an agent which upon exposure of the reagent mixture to electrochemical energy forms either a reductant or an oxidant;

(b) exposing the reagent mixture to (i) an electrochemical potential sufficient to reduce said agent to form an oxidant but not sufficient to reduce the chemical moiety to a lower oxidation state, thereby to induce said chemical moiety to electrochemiluminesce or (ii) an electrochemical potential sufficient to oxidize said agent to form a reductant but not sufficient to oxidize said chemical moiety to a higher oxidation state, thereby to induce said chemical moiety to electrochemiluminesce.

15. A method of determining the presence of an analyte of interest which binds to a chemical moiety, which comprises (a) forming a reagent mixture comprising the chemical moiety, or comprising the chemical moiety and an agent which upon exposure of the reagent mixture to electrochemical energy forms either a reductant or an oxidant, and the analyte of interest; such that the chemical moiety and the analyte specifically bind to one another, said chemical moiety having the formula $[MPL^1L^2\text{-(-link-)-}]_tB$ wherein M is a lanthanide;

P is a polydentate ligand of M ;

$L^1$ and $L^2$ are ligands of M, each of which may be a substance covalently bound to one or more of P, $L^1$ or $L^2$ through one or more covalent bond linkages, said linkages designated as (-link-) and being covalent bonds linking B with at least one of P, $L^1$ or $L^2$;

t is an integer equal to or greater than 1;

B is a biological substance, a synthetic substance which is capable of competing with a biological substance in a competitive binding reaction with a complementary material, or a non-biological substance;

P, $L^1$ or $L^2$, and B are of such number that the total number of bonds to M provided by the ligands of M equals the coordination number of m; and P, $L^1$ or $L^2$, and B are of such composition that the chemical moiety can be induced to repeatedly emit electromagnetic radiation;

(b) exposing the reagent mixture to (i) an electrochemical potential sufficient to reduce said agent to form an oxidant but not sufficient to reduce the chemical moiety to a lower oxidation state, thereby to induce said chemical moiety to electrochemiluminesce or (ii) an electrochemical potential sufficient to oxidize said agent to form a reductant but not sufficient to oxidize said chemical moiety to a higher oxidation state, thereby to induce said chemical moiety to electrochemiluminesce; and (c) detecting emitted luminescence thereby to determine the presence of the analyte of interest.

* * * * *

UNITED STATES PATENT AND TRADEMARK OFFICE
CERTIFICATE OF CORRECTION

PATENT NO.    : 5,858,676
DATED         : January 12, 1999
INVENTOR(S)   : Yang et al.

It is certified that error appears in the above-identified patent and that said Letters Patent is hereby corrected as shown below:

Column 14,
Line 66, should read -- The entire disclosure of the Kamin et al. patent is expressly incorporated herein by reference. --

Signed and Sealed this

Third Day of May, 2005

JON W. DUDAS
*Director of the United States Patent and Trademark Office*